US012728101B2

(12) United States Patent
McKean et al.

(10) Patent No.: US 12,728,101 B2
(45) Date of Patent: Sep. 8, 2026

(54) FIBROUS COMPOSITE MATERIAL

(71) Applicant: The Electrospinning Company Ltd, Didcot (GB)

(72) Inventors: Robert James McKean, Didcot (GB); Gianpaolo Bruti, Didcot (GB); Teodor-Matei Cirstea, Didcot (GB); Marco Thio, Didcot (GB); Mehri Behbehani, Didcot (GB)

(73) Assignee: The Electrospinning Company Ltd, Didcot (GB)

( * ) Notice: Subject to any disclaimer, the term of this patent is extended or adjusted under 35 U.S.C. 154(b) by 471 days.

(21) Appl. No.: 18/006,402

(22) PCT Filed: Jul. 28, 2021

(86) PCT No.: PCT/GB2021/051947
§ 371 (c)(1),
(2) Date: Jan. 23, 2023

(87) PCT Pub. No.: WO2022/023745
PCT Pub. Date: Feb. 3, 2022

(65) Prior Publication Data

US 2023/0293450 A1 Sep. 21, 2023

(30) Foreign Application Priority Data

Jul. 29, 2020 (GB) ..................................... 2011790
Jul. 29, 2020 (GB) ..................................... 2011791

(51) Int. Cl.

| | |
|---|---|
| ***A61K 9/70*** | (2006.01) |
| ***A61K 31/355*** | (2006.01) |
| ***A61K 31/505*** | (2006.01) |
| ***A61K 31/593*** | (2006.01) |
| ***A61K 31/728*** | (2006.01) |
| ***A61K 47/34*** | (2017.01) |
| ***A61P 17/02*** | (2006.01) |
| ***A61P 27/02*** | (2006.01) |

(52) U.S. Cl.
CPC .......... *A61K 9/7007* (2013.01); *A61K 31/355* (2013.01); *A61K 31/505* (2013.01); *A61K 31/593* (2013.01); *A61K 31/728* (2013.01); *A61K 47/34* (2013.01); *A61P 17/02* (2018.01); *A61P 27/02* (2018.01)

(58) Field of Classification Search
CPC ........ A61P 27/02; A61P 17/02; A61K 9/7007; A61K 31/355; A61K 31/505; A61K 31/593; A61K 31/728; A61K 47/34
See application file for complete search history.

(56) References Cited

FOREIGN PATENT DOCUMENTS

| | | | | | |
|---|---|---|---|---|---|
| CN | 1837274 | A | 9/2006 | | |
| CN | 102277737 | A | 12/2011 | | |
| CN | 107106720 | A | 8/2017 | | |
| CN | 107213505 | A | 9/2017 | | |
| KR | 10-2019-0018350 | A | 2/2019 | | |
| WO | WO/2009/042829 | A1 | 4/2009 | | |
| WO | WO/2013/172788 | A1 | 11/2013 | | |
| WO | WO-2015186101 | A1 * | 12/2015 | .......... | A61K 9/7007 |
| WO | WO/2020/070484 | A1 | 4/2020 | | |
| WO | WO-2020124072 | A1 * | 6/2020 | ............ | A61L 27/54 |

OTHER PUBLICATIONS

Shoshy Mizrahy, et al, Hyaluronan-Coated Nanoparticles: The Influence of the Molecular Weight on CD44-Hyaluronan Interactions and on the Immune Response, 156 J Control. Rel. 231 (Year: 2011).*
International Preliminary Report on Patentability issued in International Application No. PCT/GB2021/051947 dated Oct. 12, 2022.
Search & Examination Report issued in British Application No. GB2011790.9 dated Jan. 20, 2021.
Search & Examination Report issued in British Application No. GB2110879.0 dated Jan. 26, 2022.
International Search Report issued in International Application No. PCT/GB2021/051947 dated Oct. 29, 2021.
Written Opinion of the International Searching Authority issued in International Application No. PCT/GB2021/051947 dated Oct. 29, 2021.
Written Opinion of the International Preliminary Examining Authority issued in International Application No. PCT/GB2021/051947 dated Jul. 4, 2022.
Bahram, et al., "An Introduction to Hydrogels and Some Recent Applications", Emerging Concepts in Analysis and Applications of Hydrogels, Aug. 24, 2016, 9-38.
Deepthi, et al., "Chitosan-Hyaluronic Acid Hydrogel Coated Poly(Caprolactone) Multiscale Bilayer Scaffold for Ligament Regeneration", Chemical Engineering Journal, vol. 260, Sep. 9, 2014, 478-485.
Deshpande, et al., "Simplifying Corneal Surface Regeneration Using a Biodegradable Synthetic Membrane and Limbal Tissue Explants", Biomaterials, vol. 34, No. 21, Apr. 13, 2013, 5088-5106.
Dong, et al., "Electrospun Nanofibrous Materials for Wound Healing", Advanced Fiber Materials, vol. 2, No. 4, Mar. 21, 2020, 212-227.
Ekaputra, et al., "Combining Electrospun Scaffolds with Electrosprayed Hydrogels Leads to Three-Dimensional Cellularization of Hybrid Constructs", Biomacromolecules, vol. 9, No. 8, Jul. 23, 2008, 2097-2103.

(Continued)

*Primary Examiner* — Sean M Basquill
(74) *Attorney, Agent, or Firm* — Vos-IP, LLC

(57) ABSTRACT

The invention relates to a fibrous composite material comprising a nonfibrous component having a water content of less than 10 wt. %; and a fibrous component comprising a porous scaffold of a plurality of electrospun polymeric fibers; wherein the nonfibrous component is a linear or branched, water-soluble, synthetic or natural polymer dispersed on the porous scaffold; and wherein at least 50% by weight of the fibrous composite material is the fibrous component. The fibrous composite material is useful in therapy, for instance, as a synthetic or substitute amniotic membrane. It may be used in the prevention and/or treatment of various trauma induced and chronic wounds and in ophthalmology.

24 Claims, 10 Drawing Sheets

(56) References Cited

OTHER PUBLICATIONS

Ekaputra, et al., "The Three-Dimensional Vascularization of Growth Factor-Releasing Hybrid Scaffold of Poly (ε-Caprolactone)/Collagen Fibers and Hyaluronic Acid Hydrogel", Biomaterials, vol. 32, No. 32, Jul. 31, 2011, 8108-8117.
Greiner, et al., "Electrospinning: A Fascinating Method for the Preparation of Ultrathin Fibers", Angewandte Chemie International Edition, vol. 46, No. 30, Jul. 13, 2007, 5670-5703.
Hu, et al., "Advances in Crosslinking Strategies of Biomedical Hydrogels", Biomaterials Science, vol. 7, No. 3, Dec. 26, 2018, 843-855.
Huang, et al., "A Review on Polymer Nanofibers by Electrospinning and Their Applications in Nanocomposites", Composites Science and Technology, vol. 63, No. 15, Jul. 2, 2003, 2223-2253.
Jiang, et al., "Optimization and Characterization of Dextran Membranes Prepared by Electrospinning", Biomacromolecules, vol. 5, No. 2, Jan. 10, 2004, 326-333.
Kong, et al., "Electrospun Scaffolds for Corneal Tissue Engineering: A Review", Materials, vol. 9, No. 8, Jul. 27, 2016, 1-20.
Lee, et al., "In Vivo Conjunctival Reconstruction Using Modified PLGA Grafts for Decreased Scar Formation and Contraction", Biomaterials, vol. 24, No. 27, Aug. 12, 2003, 5049-5059.
Majee, Emerging Concepts in Analysis and Applications of Hydrogels, 2016, https://www.intechopen.com/books/5251.
Op 'T Veld, et al., "Design Considerations for Hydrogel Wound Dressings: Strategic and Molecular Advances", Tissue Engineering Part B: Reviews, vol. 26, No. 3, Jun. 16, 2020, 230-248.
Ramachandran, et al., "Synthetic Biodegradable Alternatives to the Use of the Amniotic Membrane for Corneal Regeneration: Assessment of Local and Systemic Toxicity in Rabbits", British Journal of Ophthalmology, vol. 103, No. 2, Oct. 18, 2018, 286-292.
Sefat, et al., "Production, Sterilisation and Storage of Biodegradable Electrospun PLGA Membranes for Delivery of Limbal Stem Cells to the Cornea", Procedia Engineering, vol. 59, Jun. 5, 2013, 101-116.
Tonsomboon, et al., "Composite Electrospun Gelatin Fiber-Alginate Gel Scaffolds for Mechanically Robust Tissue Engineered Cornea", Journal of the Mechanical Behavior of Biomedical Materials, vol. 21, Mar. 14, 2013, 185-194.
Xu, et al., "Composites of Electrospun-Fibers and Hydrogels: A Potential Solution to Current Challenges in Biological and Biomedical Field", Journal of Biomedical Materials Research Part B: Applied Biomaterials, vol. 104, No. 3, May 7, 2015, 640-656.
Liu, et al., "Electrospun PLGA/Collagen Nanofibrous Membrane as Early-Stage Wound Dressing", Journal of Membrane Science, vol. 355, Nos. 1-2, Mar. 15, 2010, 53-59.

* cited by examiner

FIBROUS COMPOSITE MATERIAL

FIELD OF THE INVENTION

The invention relates to a fibrous composite material and use thereof in therapy, in particular in ophthalmology and wound care.

BACKGROUND OF THE INVENTION

Worldwide blindness is predominantly caused by eye diseases that affect the cornea. There are estimated to be 45 million people worldwide suffering from bilateral blindness and a further 135 million suffering with severe vision impairments to both eyes. In 2001, the World Health Organisation reported that in some African regions more than 90% of all blindness cases are directly related to corneal pathology. Corneal epidemiology is complicated and encompasses a wide range of infectious and inflammatory diseases. Additionally, the severity and prevalence of corneal blindness varies from country to country and even within populations. A major cause for this is the variation in standards of ophthalmic care. Corneal blindness is not only caused by disease, but is often caused by corneal trauma, affecting 1.6 million people worldwide. In the UK alone, 2.3% of all major trauma patients are those suffering from ocular injuries. Thermal and chemical burns, caused for example by inadequate personal protective equipment, can cause severe damage to the cornea.

It is estimated that up to 2% of the population in developed nations will suffer from chronic wounds in their lifetime, driven by an aging population and unhealthy lifestyle. Type 2 diabetic patients are particularly prone to ulcerations to the lower extremities in particular. The economic burden to treat these large number of patients on healthcare providers is increasing year by year, with nearly 13 billion USD spent in the US per year. In addition, surgical wounds and trauma induced wounds further drive costs worldwide.

Grafts such as decellularised skin or amniotic membranes are commonly used to induce closure of these wounds, acting as a scaffold for the patient's own cells to restore the damaged tissue. However, procurement, storage and distribution of these grafts increase costs to healthcare. The recent Covid-19 pandemic furthermore caused tissue banks to close, creating a shortage of tissue grafts available.

Amniotic membrane, sourced from human placental tissues, has been used in the treatment of various trauma and chronical wounds, ophthalmology and other soft tissue reconstruction (i.e. tendons and capsular tissue such as the peritoneum). Indications include partial and full thickness wounds, pressure sores/ulcers, venous ulcers, diabetic ulcers, tunnelled and/or undetermined wounds, surgical-induced wounds, trauma wounds (i.e. lacerations, severe burns and abrasions) and draining wounds. Amniotic membrane comprises three layers: the epithelium, a single cell layer with surface microvilli which extend into amniotic fluid; the basement membrane, composed of reticular fibres; and the stroma, itself composed of three layers, viz. compact, fibroblast and spongy. The compact layer is the strongest layer of the amniotic membrane, capable of withstanding oedema and inflammation. The fibroblast layer contains fibroblasts dispersed amongst reticular tissue and may provide a phagocytic benefit. The spongy layer is the outermost layer and is typically gelatinous, containing bundles of reticulin in mucins, and serves to reduce frictional forces between the amniotic membrane and the adjacent tissue or substance.

Amniotic membrane, sourced from human placental tissues, has been used in ophthalmology for over two decades for the treatment of a number of conditions, such as cicatricial pemphigoid and Stevens-Johnson syndrome, pterygium, persistent epithelial defects with ulceration, conjunctival surface reconstruction, and ocular surface reconstruction in patients with chemical and thermal burns.

Amniotic membrane is known to have low immunogenicity, which makes it ideal for tissue reconstruction. The ability to freeze and thereby preserve sections of amniotic membrane has further increased its clinical appeal.

There are a number of disadvantages to using amniotic membranes, for instance that in developing countries tissue procurement and processing is unregulated, pressing availability of the tissue for clinical use. Furthermore, in severely inflamed tissue, rejection of the material by the host can occur. In addition, as the product of human donors there is an inherent inconsistency in the supply of amniotic membrane for use and differences between tissues from different donors, which can affect product performance. Furthermore, while amniotic membrane can be harvested and cryopreserved, the equipment necessary for safe storage is typically not available and ill-adapted for use in developing countries with a lower level of medical infrastructure.

Therefore, there is a desire to develop materials which are standardised and safe. Such materials from non-human sources are known as synthetic or substitute amniotic membranes (SAMs).

In order to successfully use a SAM in the treatment of beforementioned wounds, it must be flexible, pliable and conform to the shape of the wound bed. Similarly, in order to successfully use a SAM in ophthalmic surgeries, it must be flexible, pliable and fit around the curvature of the eye. Preliminary work has shown that poly(lactide-co-glycolide) (PLGA) membranes were pliable and soft when freshly spun with HFIP solvent but became brittle when solvent was removed. This device has been previously described in Deshpande et al., "Simplifying corneal surface regeneration using a biodegradable synthetic membrane and limbal tissue explants", *Biomaterials,* 2013, 34, 5088-5016 and Ramachandran et al., "Synthetic biodegradable alternatives to the use of the amniotic membrane for corneal regeneration-assessment of local and systemic toxicity in rabbits", Br. J. Ophthalmol., 2019, 103, 286-292.

SUMMARY OF THE INVENTION

In accordance with the first aspect of the invention, there is provided a fibrous composite material comprising

- a non-fibrous component having a water content of less than 10 wt %; and
- a fibrous component comprising a porous scaffold of a plurality of electrospun polymeric fibres;
- wherein the non-fibrous component is a linear or branched, water-soluble, synthetic or natural polymer dispersed within the porous scaffold; and
- wherein at least 50% by weight of the fibrous composite material is the fibrous component.

In accordance with a second aspect of the invention, there is provided a process for making a fibrous composite material according to the first aspect of the invention, comprising simultaneously depositing a non-fibrous component while electrospinning a plurality of polymeric fibres to form the fibrous composite material on a collector.

In accordance with a third aspect of the invention, there is provided a fibrous composite material according to the first aspect of the invention, for use in therapy.

In accordance with a fourth aspect of the invention, there is provided a method of treatment of a patient in need thereof, comprising administering a fibrous composite material according to the first aspect of the invention to a patient.

In accordance with a fifth aspect of the invention, there is provided a use of a fibrous composite material according to the first aspect of the invention in the manufacture of a medicament for use in therapy.

The materials of the present invention address the shortcomings in the prior art. When used as a SAM, the risk of cross-contamination from donors is removed whilst enhancing reliability and standardisation between batches of membrane, thereby reducing the risk for the product not performing in the clinic. The SAMs of the invention achieve good cell adhesion and possess appropriate mechanical properties (e.g. tensile strength) to allow them to be applied to the cornea, wound bed or other bodily location. The SAMs also advantageously biodegrade to leave behind the formed tissues.

The use of electrospun materials for wound care application is well documented in the literature. For example, Dong et al. (Electrospun Nanofibrous Materials for Wound Healing, Advanced Fiber Materials (2020)) offers an overview of the current state-of-the-art of the use of electrospun materials for wound healing. The authors highlight the need for further work in this field as the cell integration into electrospun nanofibrous materials needs to be improved, as well as more progress is required in controlling the release profile of such materials when it comes to therapeutic additives. The incorporation of a dry, polymeric component in the present invention allows for a greater control over the spacing between electrospun fibres. It further enables the controlled release of added therapeutics through the use of the dry, non-fibrous component.

The use of hydrogels as wound care dressings is a standard material used in current procedures. Op't Veld et al. (Design Considerations for Hydrogel Wound Dressings: Strategic and Molecular Advances. Tissue Engineering Part B: Reviews 26, 230-248 (2020)) summarises the current state-of-the-art in the use of hydrogels wound dressings. These hydrogels are used in a number of existing devices for wound healing, but the authors highlight their shortcomings in terms of design considerations. One of the current drawbacks of these materials is that many of their properties are linked to their structure, including, but not limited to, shelf-life, mechanical integrity and degradation rate. This means compromises need to be made when designing a hydrogel based wound dressing as some properties are oppositely correlated to the chemical and physical structure of these hydrogels. The present invention offers an advantage over hydrogel-based wound dressings as the dry-polymeric component is not a hydrogel but can behave similarly once deployed. Since at least 50% of the composition by weight is the fibrous component, it can generate the necessary mechanical integrity of the whole device for use in wound dressings. The dry-polymeric component can be tailored to possess optimal properties without having to also offer the mechanical integrity needed in a classical hydrogel-based wound dressing.

A variety of other materials suitable for tissue engineering have been described in the literature. For instance, Ekaputra et al. ("The three-dimensional vascularisation of growth factorreleasing hybrid scaffold of poly (ε-caprolactone)/collagen fibers and hyaluronic acid hydrogel", *Biomaterials,* 2011, 32, 8108-8117) discloses PCL-collagen fibres comprising a hyaluronic acid hydrogel formed by dual electrospinning. It differs from the present invention in that a hydrogel is present, formed from a mix of thiol-modified hyaluronic acid thiol-modified heparin, accelerated by the addition of collagen. The resulting product, due to the hydrogel, is wet. In contrast, the composite material of the first aspect of the invention is dry and therefore not a hydrogel, as the presence of any liquid would induce degradation and reduce the shelf life of the product.

Jiang et al. ("Optimization and Characterization of Dextran Membranes Prepared by Electrospinning", *Biomacromolecules,* 2004, 5, 326-333) discloses composite electrospun membranes formed from a mixed solution of PLGA and dextran. It does not disclose the incorporation of hyaluronic acid into the electrospun material. A significant difference to the present invention is that the location of the dextran cannot be controlled precisely, as a mixed electrospinning solution is used. In contrast, the present invention affords the ability to control the position of hyaluronic acid, allowing it to be present on the surface of the fibres and to move freely throughout the electrospun polymer scaffold without requiring the scaffold to degrade to release it.

Lee et al. ("In vivo conjunctival reconstruction using modified PLGA grafts for decreased scar formation and contraction", *Biomaterials,* 2003, 24, 5049-5059) discloses PLGA grafts for corneal repair comprising a porous block of PLGA polymer which is produced by casting a solution of PLGA enriched with salt, which is then washed to remove the salt, leaving pores behind in the block. The resulting product is not produced by electrospinning and does not comprise fibres.

Tonsonboom et al. ("Composite electrospun gelatin fiber-alginate gel scaffolds for mechanically robust tissue engineered cornea", *J. Mech. Behav. Biomed.,* 2013, 21, 185-194) discloses fibre-reinforced hydrogels, wherein gelatin mats are immersed in an alginate hydrogel, prompting the gelatin fibres to be infiltrated by alginate. This forms a product which is wet, wherein the crosslinked hydrogel occupies pores in the fibre network, and which can be stored in water until needed. In contrast, the material according to the first aspect of the present invention is not wet, and hyaluronic acid is dispersed along the fibres thereof. The hyaluronic acid which can be used in the present invention does not form a hydrogel in its dry form—instead, in some embodiments, it is able to dissolve and spread beyond the fibrous scaffold to impart greater lubricity to the membrane.

WO2013/172788 discloses fibre-reinforced hydrogel composites and methods of their formation, wherein the composite comprises a plurality of short electrospun fibres dispersed within the hydrogel without long-range order. In contrast, the present invention utilises significantly longer electrospun fibres on which smaller quantities of hyaluronic acid are dispersed.

WO2015/186101 discloses a wound dressing comprising a non-fibrous component (hyaluronic acid and alginate) which is lyophilised and a fibrous component formed from electrospun fibre mats. The non-fibrous component forms the predominant material in this wound dressing.

In contrast to the materials above, the present invention offers significant advantages. It is easy to handle, flexible, pliable and demonstrates excellent suturability. Crucially, when wet in use, the material is transparent, which is important for the intended use. Moreover, this transparency is achieved without needing to use ionic gas plasma treatment of the material, advantageously simplifying its manufacture. In addition, the material is not cytotoxic, demonstrating its safety for surgical use.

DETAILED DESCRIPTION OF THE INVENTION

Figure 1A:
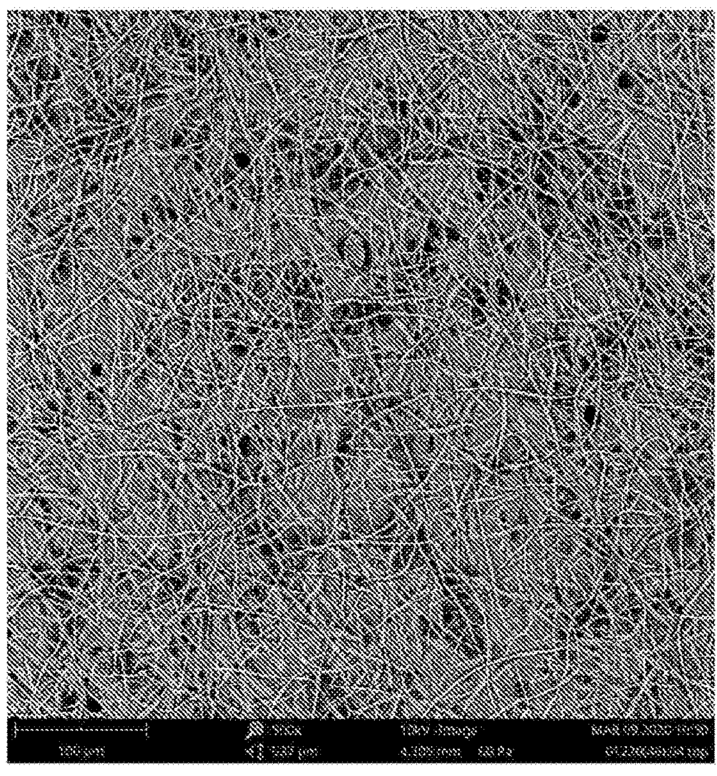
FIGS. 1A, 1B and 1C show scanning electron micrographs of a fibrous composite material according to the present invention comprising a PLGA membrane reinforced with HA at 500×, 1000× and 2000× magnification.
Figure 1B:
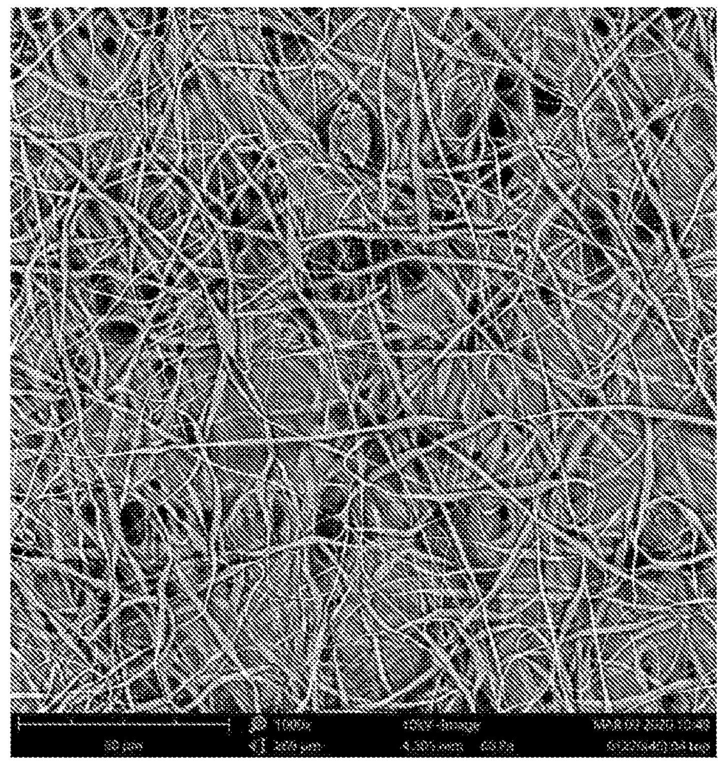
Figure 1C:
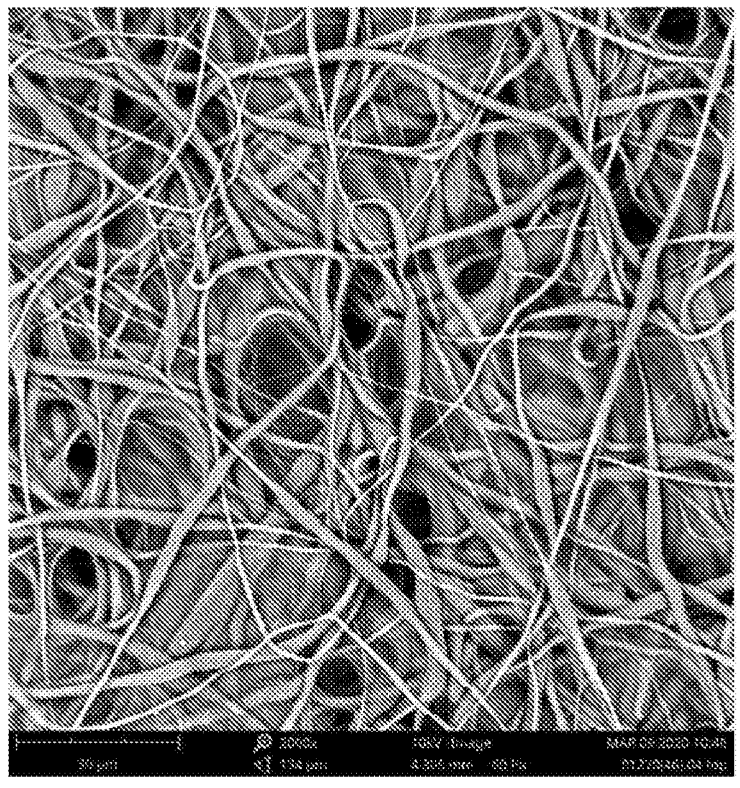

The fibrous composite material comprises a non-fibrous component and a fibrous component comprising a porous scaffold of a plurality of electrospun polymeric fibres. The fibrous component of the fibrous composite material is produced by electrospinning and forms a non-woven mat. Electrospun fibres provide a superior means of achieving membranes or scaffolds, and electrospinning is both simple and reliable. The process of electrospinning is further described in the review articles by Huang et al., *Compos Sci and Technol.,* 2003, 63, 2223-2253 and Greiner and Wendorff, *Angew. Chem. Int. Ed.,* 2007, 46, 5670-5703. We have described suitable electrospinning processes in our previous patent applications, for instance, published as WO 2020/070484.

The fibrous composite material may take a variety of shapes and forms. In some embodiments of the invention, the fibrous composite material forms a membrane, preferably a biocompatible membrane. It may be shaped for application to various parts of the human or animal body, as further detailed below.

The non-fibrous component is a non-fibrous polymeric component and is typically a linear or branched, water-soluble, synthetic or natural polymer dispersed on and within the pores of the porous scaffold. The linear or branched, water soluble polymers may be selected from naturally-occurring polymers such as polysaccharides and/or the salts thereof, examples of which include, but are not limited to, hyaluronic acid, starch, dextran, heparin, chondroitin sulfate, dermatan sulfate, heparan sulfate, keratan sulfate, dextran sulfate, pentosan polysulfate, and chitosan; and protein (and other polyamino acids), examples of which include but are not limited to gelatin, collagen, fibronectin, laminin, albumin, elastin, and active peptide domains thereof; and alginic acids and their alkali metal salts, said alginic acids consisting of various copolymer segments of D-mannuronic acid and L-glucuronic acid, depending upon their natural origin as well as other carrageenan types which comprise linear polysaccharides of alternating 1,3-linked β-D-galactopyranosyl and 1,4-linked α-D-galactopyranosyl units.

The linear or branched, water soluble polymers may be synthetic polymers and/or salts thereof, examples which include, but are not limited to, polyvinylpyrrolidone (PVP), polyethylene glycol (PEG), polyacrylamide (PAA), polyvinyl alcohol (PVA), polyacrylic acid (PAAc), poly methyl vinyl ether (PMVE) and the like, as well as blends and copolymers thereof.

In a preferred embodiment, the non-fibrous component comprises hyaluronic acid (HA). Preferably the hyaluronic acid is a high molecular weight hyaluronic acid. Preferably, the molecular weight is greater than 300 kDa, for instance greater than 400 kDa, most preferably greater than 500 kDa. Suitably, the hyaluronic acid has a molecular weight from 500 kDa to 10,000 kDa.

High molecular weight hyaluronic acid has been shown to have an anti-inflammatory effect, skewing resident macrophages in a wound bed from a pro-inflammatory phenotype (M1), towards a reconstructive phenotype (M2). This crucial switch results in improved attachment and growth of epithelial cells, facilitate tissue granulation and subsequent wound closure. Furthermore, high molecular weight hyaluronic acid is a component of human amniotic membrane, thus further demonstrating its suitability for use in this invention.

The non-fibrous component may be crosslinked. The crosslinking procedure is well known to any person skilled in the art. For instance, an overview of the general methods for crosslinking can be found in Hu et al., "Advances in crosslinking strategies of biomedical hydrogels", Biomater. Sci., 2019, 7, 3, 843-855. The crosslinking may be by physical or chemical means.

Suitable physical methods of crosslinking the non-fibrous, polymeric component include, but are not limited to, crosslinking by ionic/electrostatic interactions, crosslinking by hydrophobic interactions, crosslinking by thermal induction based on lower critical solution temperature/upper critical solution temperature, crosslinking by ultrasonic induction, crosslinking by crystallisation, crosslinking by hydrogen bonding, crosslinking by metal coordination and crosslinking by host-guest interactions.

Suitable chemical methods of crosslinking the non-fibrous, polymeric component include, but are not limited to, crosslinking by photopolymerization, crosslinking by enzyme catalysed reactions, crosslinking by click chemistry, crosslinking by Diels-Alder reaction, crosslinking by Schiff base formation, crosslinking by oxime crosslink, crosslinking by Michael addition and crosslinking by dynamic covalent chemistry.

In the first aspect of the invention, the non-fibrous component has a water content of less than 10 wt %, measured with respect to the weight of the non-fibrous component. Accordingly, it can be referred to as a "dry non-fibrous component." The non-fibrous component is therefore not a hydrogel in its dry form, as by definition, water must constitute at least 10% of the total weight (or volume) for a material to be a hydrogel (Bahram, M. et al., 2016, "An Introduction to Hydrogels and Some Recent Applications", in Emerging Concepts in Analysis and Applications of Hydrogels, ISBN 978-953-51-2510-5, DOI: 10.5772/64301). However, the non-fibrous component may form a hydrogel when it is wetted, for instance, in use. Thus, the dry non-fibrous component may alternatively be referred to as a hydrogel precursor.

In a preferred embodiment, the non-fibrous component is not crosslinked.

In further preferred embodiments of the invention, the non-fibrous polymeric component has a water content less than 7 wt %, preferably less than 6 wt % or 5 wt %, for instance less than 4 wt %, for instance less than 3 wt % or most preferably less than 2 wt %.

The water content of a material can be measured by thermogravimetric analysis (TGA), which is described in detail in the ISO standard ISO 11358-1:2014. This method uses a drying oven, and the weight of the material is measured before and after drying. In order to measure the water content in the sample, the weight loss at around 100° C. is taken to be the overall amount of evaporated water contained in the sample. This weight can then be related to the overall weight of the fibrous composite material to obtain the percentage of water relative to both the fibrous and non-fibrous components.

Preferably, the fibrous composite material in its entirety also has a low water content. Preferably, the water content of the fibrous composite material is less than 10 wt %, preferably less than 7 wt %, for instance less than 6 wt % or 5 wt %, for instance less than 4 wt %, for instance less than 3 wt % or most preferably less than 2 wt %. This water content can also be measured by TGA.

The other component of the fibrous composite material is the fibrous component. The fibrous component comprises (makes up) at least 50% by weight of the fibrous composite material, preferably at least 60%, even more preferably at least 70%, 75% or at least 80%, 85% or 90% by weight of the fibrous composite material. The relative proportions of the fibrous and nonfibrous components which make up the fibrous composite material can be determined by calculation. For instance, in the process used to form the fibrous composite material, the mass transfer of material component is known through the polymer flow rate used. From this, it is possible to calculate the ratio of deposited polymeric fibrous to non-fibrous component. The calculation uses the flow rate of the components and the polymer concentration in solution. An example of such a calculation is given in the Examples section.

Preferably, the fibrous component has a water content of less than 10 wt %, for instance less than 7 wt % or less than 6 wt % or 5 wt %. Preferably the water content of the fibrous component is less than 4 wt %, for instance less than 3 wt % or most preferably less than 2 wt %. In an embodiment, the water content of the fibrous component is low enough such that when the fibrous component is incorporated in a fibrous composite material, the water content of the fibrous composite material is minimised.

In some embodiments, the fibrous component comprises fibres of length more than 1000 μm (1 mm). In some embodiments, the fibres have a length greater than 2 mm, for instance, greater than 5 mm or 10 mm.

In some embodiments, the fibres of the fibrous composite material have a diameter in the range from 500 nm to 10 μm, or from 750 nm to 8 μm, or from 1 μm to 7 μm, or from 2 μm to 5 μm, or from 3 μm to 4 μm. Typically, the length and mean diameter of the polymer fibres in the scaffold is measured by Scanning Electron Microscopy (SEM).

These dimensions refer to an individual fibre or the mean average of all the fibres in the composition.

In some embodiments, the fibrous component comprises a biodegradable polymer. The polymer is preferably a biocompatible polymer. The polymer is preferably non-cytotoxic.

In some embodiments, the fibrous component comprises poly(L-lactide); poly(glycolic acid); polyhydroxybutyrate; polystyrene; polyethylene; polypropylene; poly(ethylene oxide); a poly(ester urethane); poly(vinyl alcohol); polyacrylonitrile; polylactide; polyglycolide; polyurethane; polycarbonate; polyimide; polyamide; aliphatic polyamide; aromatic polyamide; polybenzimidazole; poly(ethylene terephthalate), poly[ethylene-co-(vinyl acetate)]; poly(vinyl chloride); poly(methyl methacrylate); poly(vinyl butyral); poly(vinylidene fluoride); poly(vinylidene fluoride-co-hexafluoropropylene); cellulose acetate; poly(vinyl acetate); poly(acrylic acid); poly(methacrylic acid); polyacrylamide; polyvinylpyrrolidone; poly(phenylene sulfide); hydroxypropylcellulose; polyvinylidene chloride, polytetrafluoroethylene, a polyacrylate, a polymethacrylate, a polyester, a polysulfone, a polyolefin, polysilsesquioxane, silicone, epoxy, cyanate ester, a bis-maleimide polymer; polyketone, polyether, polyamine, polyphosphazene, polysulfide, an organic/inorganic hybrid polymer or a copolymer thereof, for instance, poly(lactide-co-glycolide); polylactide-co-poly(ε-caprolactone) or poly(L-lactide)-co-poly(ε-caprolactone); or a blend thereof, for instance a blend of poly(vinyl alcohol) and poly(acrylic acid). In a preferred embodiment, the fibrous component comprises poly(lactide-co-glycolide), otherwise known as PLGA.

In a preferred embodiment, the fibrous component comprises PLGA, wherein the molecular weight of the PLGA is preferably in the range 10 kDa to 5 MDa. Preferred ratios of the lactide to glycolide component are as follows: 95:5, 90:10, 85:15, 80:20, 75:25, 70:30, 65:35, 60:40, 55:45, 50:50, 45:55, 40:60, 35:65, 30:70, 25:75, 20:80, 15:85, 10:90 and 5:95.

In a preferred embodiment of the invention, the dry polymeric (non-fibrous) component comprises hyaluronic acid (HA) and the fibrous component comprises PLGA.

In one particularly preferred embodiment, there is 10-20 wt % HA and 80-90 wt % PLGA.

The network of fibres forming the fibrous component is a random distribution of fibres in space that forms an interconnecting net with spacing between the fibres. Such a distribution is formed by the electrospinning process used to deposit the fibrous component. The network has small spaces between the fibres comprising the network, forming pores or channels in the network, which allow fluid to pass through.

The porous network of fibres is a non-woven network, i.e. the fibre is typically randomly orientated in the porous network. Thus, the polymer fibres in the porous, non-woven network of fibres do not have any particular orientation, i.e. the fibre in the porous, non-woven network is typically randomly orientated or at least approaching random orientation. The degree of alignment of the polymer fibres in the membrane is therefore low.

The fibrous component forms a porous scaffold. In some embodiments, the porosity of the fibrous composite material can be 50%, 60%, 70%, preferably 80% or most preferably 90%.

The porosity, average pore diameter and the average fibre diameter of a non-woven network are interrelated, as explained for instance in Greiner and Weddorff, Angew. Chem. Int. Ed. 2007, 46, 5670-5703.

The components in the fibrous composite material may be physically mixed together to form the composite. By the term "physically mixed", it is meant that the non-fibrous component and the fibrous component are dispersed in one another, and do not chemically react to form a new material.

The fibrous and the dry non-fibrous component are generally not covalently linked. This allows the non-fibrous component to "slip over" the fibrous component. The non-fibrous component can move independently of the fibrous component such that the fibrous component need not degrade or modify its structure to release the non-fibrous component. In practice, this results in the spread of the non-fibrous component across and around the fibrous component, which acts as a scaffold.

The non-fibrous component is dispersed within the pores of the fibrous porous scaffold. It may also be dispersed on fibrous porous scaffold.

Electrospinning is used to produce the fibrous component, and this produces a non-woven network of polymer fibres with a large degree of porosity. Due to the nature of the process there are generally no isolated, unconnected pores present in an electrospun material. The void space between the fibres can be described as a large pore. In the present invention, the fibrous component has a non-fibrous component dispersed within its pore space. The volumetric fraction of the non-fibrous component with respect to the fibrous component can be calculated by first measuring the physical dimensions of the composite material. In a next step, the relative weights of each component are measured and converted to volume by using the density of the constituents. This allows the person skilled in the art to then calculate the volume fraction of each component as well as the empty space not occupied by either component in the material.

Regarding the volume proportion of the pores filled by non-fibrous component, this proportion typically lies in the range 10-30%, or alternatively in the range 12.5-27.5%, or in the range 15-25%, or in the range 17.5%-22.5%.

When in use, the fibrous composite material may absorb water. For instance, the non-fibrous component may absorb water and, in some embodiments (particularly when the non-fibrous component is not cross-linked or only partly cross-linked), may leach out of the fibrous component. This may provide lubrication to the fibrous composite material, which may improve the physical characteristics of the final product, contributing to keeping the wound bed hydrated.

The fibrous component of the invention is formed by electrospinning. In a process according to this invention, a fibre (preferably, a nanofibre) precursor solution is electrospun onto a collection substrate to produce a scaffold comprising a non-woven network of polymer fibres; wherein the fibre precursor solution comprises a polymer dissolved in a solvent. The network of polymer fibres can comprise a single layer of fibres or multiple (two or more) layers. The electrospinning process can easily be adapted to produce scaffolds having multi-layered structures.

To produce the fibrous composite material of the invention, the nonfibrous polymeric material is deposited at the same time as the fibrous component is being electrospun. In an embodiment, the nonfibrous polymeric material is deposited by spraying, or more preferably by electrospraying. The materials are cosprayed/spun onto a collector where the composite fibrous material forms. In order to assist the spraying process, the nonfibrous polymeric material is dissolved in a solvent before it is sprayed. In some embodiments, the solvent used to spray the polymeric material is a polar protic solvent. In some embodiments, the solvent is selected from 1-methyl-2-pyrrolidinone, 1-pentanol, 2-ethoxyethanol, 2-ethoxyethyl acetate, 2-nitropropane, 2,2,2-trifluoroethanol, acetic acid, acetone, acetonitrile, aniline, butanol, carbon tetrachloride, chloroform, cyclohexanone, di(ethylene glycol), diacetone alcohol, dichloroethane, dichloromethane, diethyl ether, diethylene glycol monoethyl ether, diisopropyl ether, dimethylacetamide, dimethylformamide, dimethyl sulfoxide, dioxane, ethanediol, ethanol, ethyl acetate, formic acid, glycerol, hexafluoropropan-2-ol, isopropanol, methanol, methyl acetate, methyl ethyl ketone, morpholine, n-butyl acetate, n-propanol, propylene carbonate, tetrahydrofuran, trifluoroacetic acid, water, or a mixture thereof. In a preferred embodiment, the solvent is a water/methanol mixture. The solvent evaporates at the end of the spraying process to leave the dry nonfibrous polymeric material in the fibrous composite material. The use of the cospraying/spinning method advantageously gives the final composite material its final porous structure, with nonfibrous polymeric material deposited on and within the porous scaffold.

A solvent is also used to electrospin the fibrous component. In some embodiments, the solvent is selected from 1-methyl-2-pyrrolidinone, 1-pentanol, 2-ethoxyethanol, 2-ethoxyethyl acetate, 2-nitropropane, 2,2,2-trifluoroethanol, acetic acid, acetone, acetonitrile, aniline, butanol, carbon tetrachloride, chloroform, cyclohexanone, di(ethylene glycol), diacetone alcohol, dichloroethane, dichloromethane, diethyl ether, diethylene glycol monoethyl ether, diisopropyl ether, dimethylacetamide, dimethylformamide, dimethyl sulfoxide, dioxane, ethanediol, ethanol, ethyl acetate, formic acid, glycerol, hexafluoropropan-2-ol, isopropanol, methanol, methyl acetate, methyl ethyl ketone, morpholine, n-butyl acetate, n-propanol, propylene carbonate, tetrahydrofuran, trifluoroacetic acid, water, or a mixture thereof. In a preferred embodiment, the solvent is a polar aprotic solvent.

Plasma treatment can optionally be employed as a final step in the manufacture of the fibrous composite material. This can enhance the beneficial properties of the material, including inter alia its transparency. In some embodiments the plasma treatment can involve treatment with an organic plasma. In some embodiments the organic plasma is acrylic acid plasma.

The product of the above processes is generally a large electrospun sheet of material. This can be processed to smaller parts of appropriate size and shape using techniques such as laser cutting, guillotine cutting, die cutting, and cutting with a blade or scissors. The product may be cut into circular, rectangular or square shapes. Dimensions of a square may be for instance from 3×3 cm to 25×30 cm.

In a further embodiment, there is provided a fibrous composite material comprising

- a non-fibrous component having a water content of less than 10 wt %; and
- a fibrous component comprising a porous scaffold of a plurality of hydrodynamically spun polymeric fibres;
- wherein the non-fibrous component is a linear or branched, water-soluble, synthetic or natural polymer dispersed within the porous scaffold; and wherein at least 50% by weight of the fibrous composite material is the fibrous component.

In this embodiment, the fibrous component is manufactured using a hydrodynamic spinning method. Hydrodynamic spinning may be defined as the production of polymer fibres using a liquid, for instance in the form of a polymer solution, a polymer melt or a gel-polymer, through the application of an external force and the optional use of a spinneret. Common hydrodynamic spinning methods known to a person skilled in the art include, but are not limited to, melt spinning, dry spinning, wet spinning and extrusion, solution spinning, force spinning, electrospinning, melt blowing, gas-assisted spinning and centrifugal spinning. Polymer fibres created by such methods are hereinafter referred to as being "hydrodynamically spun".

In a further embodiment, there is also provided a process for making a fibrous composite material according to the above embodiment, comprising simultaneously depositing a non-fibrous component while hydrodynamically spinning a plurality of polymeric fibres to form the fibrous composite material on a collector.

There is also provided a fibrous composite material according to the above embodiment for use in therapy, preferably in wound care.

There is also provided a method of treatment of a patient in need thereof, comprising administering to the patient a fibrous composite material according to the above embodiment.

The preferred features as discussed above in the context of the invention also apply to these embodiments wherein the fibrous component is manufactured by electrospinning. For instance, the preferred hydrodynamic spinning method is electrospinning.

The material according to the invention is a fibrous composite material comprising electrospun fibres and a non-fibrous polymeric component which is suitable for use in a therapeutic application. Thus the fibrous composite material may be a therapeutic composition. The therapeutic application may be tissue repair. Accordingly the fibrous composite material may be provided in the form of a replacement tissue patch.

Two particularly preferred uses of the invention lie in wound care and ophthalmology. Defects of the cornea behave in a similar manner to wounds. Both the cornea and skin provide a barrier to the outside world and have developed intrinsic and similar mechanisms to protect the organism to external threats and dangers. Both tissues are capable of rapidly restoring any damage through regenerative processes that are based on similar biological mechanisms. Studies performed on skin have laid the foundation of cornea regeneration.

Suitable therapeutic uses include use in wound care, more specifically partial and full thickness wounds, pressure sores/ulcers, venous ulcers, diabetic ulcers, tunnelled and/or undetermined wounds, surgical-induced wounds, trauma wounds (i.e. lacerations, severe burns and abrasions) and draining wounds. The material may alternatively act as a scaffold to support therapies using skin stem cell transplantation.

The material may be used as a synthetic or substitute amniotic membrane. For instance, the material may be applied as a graft to a wound bed. Before applying to the wound bed, the fibrous composite material may be cut to an appropriate size and shape. Cells may grow over the graft. Alternatively, the material may be used in conjuncture with allo-/xenogenic grafts to provide additional support or be used as an interface layer.

Unlike a natural amniotic membrane, there is no directionality to the material of the present invention when used as a SAM (one of its advantages). When inserted onto the wound bed, it functions as a substrate to resident epithelial cells to grow, thereby aiding the re-epithelisation of the epithelium, granulation of the tissue and wound closure.

After application to the wound bed, the material can adapt its shape to the surface of the wound bed. It can alternatively be fixed into place through the use of suture or glues such as fibrin glue or cyanoacrylate glue.

The material can be provided in different thicknesses to address different clinical indications. For instance, the thickness of the material may range from 20 μm to 2 mm, for instance, 30 μm to 1 mm. It is desirable that the material has a shelf-life of at least six months at room temperature (20° C.). It is preferred that the material is terminally sterilised in its final packaging.

The fibrous composite material of the invention preferably biodegrades when in use over a suitable biological timeframe. For wound care use, the material can be designed to degrade within a time span of 2 to 24 weeks.

In a different embodiment, there is provided a fibrous composite material according to the above embodiment for use in ophthalmology. Suitable therapeutic uses include use in ophthalmology, for instance, the prevention or treatment of ocular disorders, for instance corneal disorders or defects. Accordingly, the material may be provided in the form of an ocular patch, for instance, a corneal patch. The material may be used to prevent and/or treat persistent epithelial defect, ocular complications associated with Stevens-Johnson syndrome, primary/recurrent pterygia, cicatricial pemphigoid and conjunctival forniceal reconstruction, corneal ulcers, corneal erosion, acute chemical/thermal burns, post-infectious keratitis (herpetic, vernal, bacterial), pinguecula, symblepharon, conjunctivoplasty or painful bullous keratopathy. The material may alternatively act as a scaffold for transfer of limbal stem cells for patients with limbal stem cell deficiency. A further use is the removal of epithelial or subepithelial lesions (for instance, band keratopathy, scars and tumours). The material may be used to cover defects after removal of large conjunctival lesions. Further uses include bleb revisions and scleral thinning.

The material may be used as a synthetic or substitute amniotic membrane. For instance, the material may be applied as a graft to an eye. Before applying to the eye, the fibrous composite material may be cut to an appropriate size and shape. Cells may grow over the graft. Alternatively, the material may be used as a bandage applied onto the ocular defect. In such use, cells do not generally grow along the material and the material instead fulfils a protective role to support self-healing.

Unlike a natural amniotic membrane, there is no directionality to the material of the present invention when used as a SAM (one of its key advantages). When inserted into the ocular defect it can provide corneal and conjunctival epithelial cells with a substrate on which to grow, thereby aiding the re-epithelisation of the epithelium of the host.

After application to the eye, the material can adapt its shape to the curvature of the eye. It can alternatively be sutured in place. The material of the invention is particularly suited for suturing. It may alternatively be applied to the eye by gluing. The glue used can be fibrin glue.

The material can be provided in different thicknesses to address different clinical indications. For instance, the thickness of the material may range from 20 μm to 500 μm. It is desirable that the material has a shelf-life of at least six months at room temperature (20° C.). It is preferred that the material is terminally sterilised in its final packaging.

The fibrous composite material of the invention preferably biodegrades when in use over a suitable biological timeframe. For ophthalmic use, preferably the material degrades within 8 weeks.

In some embodiments, the fibrous composite material is mixed with a liquid carrier before being administered to a patient. Suitable liquids include saline. In some embodiments, the fibrous composite material can be combined with one or more additives. The additives may be mixed with the liquid carrier, or may be added to the fibrous composite material during its manufacture.

In some embodiments, the one or more additives can comprise therapeutics, active ingredients or ingredients with additional properties that are beneficial when the fibrous composite material is applied to the patient.

The therapeutic composition described herein comprises the fibrous composite material and may further comprise cells, a biomolecule or other active agent. The biomolecule or other active agent may be a drug, a nucleic acid, a nucleotide, a protein, a polypeptide, an antibody or an exosome. The nucleic acid may comprise DNA, RNA, RNAi, saRNA or siRNA. Optionally, the therapeutic composition comprises cells, for instance adherent therapeutic cells, and the fibrous composite material. The cells may be disposed within the porous network of fibres in the scaffold. The cells may be disposed in pores of the scaffold. The cells may be disposed on (e.g. may adhere to) the surface of the scaffold. The cells may be disposed in pores of the scaffold and may also be disposed on (e.g. may adhere to) the surface of the scaffold.

The therapeutic composition of the invention may further comprise additives, preferably mixed with the fibres of electrospun material. Such additives may include growth factors such as vascular endothelial growth factor (VEGF). An additive may alternatively be an oxygen-releasing material such as $CaO_2$ or haemoglobin. Alternative additives include crosslinking agents, for instance, calcium ions for the crosslinking of hydrogel precursors. Suitable additives may be selected from the following: haemoglobin, peroxides (for instance, $H_2O_2$, $CaO_2$, $MgO_2$, $Li_2O_2$, $Na_2O_2$), sodium percarbonate ($Na_2CO_3$), perfluorocarbons, hydroxyapatite, tricalcium phosphate (bone growth promoting materials), growth factors, catalase and other enzymes.

Other additives may include, in some embodiments, antimicrobials, antivirals, antifungals, and/or silver nanoparticles. In some embodiments, the additives comprise a vitamin, for instance vitamin D, vitamin E, or another substance, such as ectoine. In some embodiments, the one or more additive comprises a hyaluronate salt. In a preferred embodiment, the hyaluronate salt is sodium hyaluronate.

Suitable therapeutics include antibiotics (e.g. fluoroquinolones, aminoglycosides, polymyxin B Combinations), steroids, miotics, antifungal agents, antiangiogenic agents, anti-inflammatory agents, lubricants and proteins (e.g. epithelial growth factor, nerve growth factor).

Examples of growth factors may include any one or more of the following: Colony Stimulating Factors (m-CSF, G-CSF, GM-CSF), Epidermal growth factor (EGF), Erythropoietin (EPO), Fibroblast growth factor (FGF), Hepatocyte growth factor (HGF), Hepatoma-derived growth factor (HDGF), interleukins, Keratinocyte growth factor (KGF), Migration-stimulating factor (MSF), Macrophage-stimulating protein (MSP), also known as hepatocyte growth factor-like protein (HGFLP), Myostatin (GDF-8), Neuregulins (e.g. Neuregulin 1, 2, 3 or 4), Neurotrophins (e.g. Brain-derived neurotrophic factor (BDNF), Nerve growth factor (NGF), Neurotrophin-3 or 4), Placental growth factor (PGF), Platelet-derived growth factor (PDGF), Renalase (RNLS), T-cell growth factor (TCGF), Thrombopoietin (TPO), Transforming growth factors such as Transforming growth factor alpha (TGF-α) or beta (TGF-β), Tumour necrosis factor-alpha (TNF-α), Vascular endothelial growth factor (VEGF) or factors involved in the Wnt Signalling Pathway. Also preferred are cytokines including the interleukins mentioned above.

Often, the cells in the therapeutic composition of the invention comprise adherent therapeutic cells. Adherent cells are cells which are capable of adhering to culture vessels which have been specifically treated for the culture of adherent cells. The concept of adherent cells is well known to a person skilled in the art. The skilled person is capable of identifying whether or not cells are adherent. Therapeutic cells are cells which are capable of having a therapeutic effect. Therapeutic cells are typically living cells. Therapeutic cells are typically cells which are capable of repairing damaged or diseased tissue. The therapeutic cells are preferably autologous. In other words, the cells are preferably derived from the patient into whom the cells will be administered to repair damaged or diseased tissue. Alternatively, the cells are preferably allogeneic. In other words, the cells are preferably derived from a patient who is immunologically compatible with the patient into whom the cells will be administered to repair damaged or diseased tissue. The cells may be semi-allogeneic. Semi-allogeneic populations are typically produced from two or more patients who are immunologically compatible with the patient into whom the cells will be administered. In other words, all of the cells are preferably genetically identical with the patient into whom they will be administered or sufficiently genetically identical that the cells are immunologically compatible with the patient into whom they will be administered. Cells may be genetically engineered to be compatible to the host's immune system, so that the host's immune system does not attack the cells.

The composition typically comprises more than one cell, such at least about 2, at least about 5, at least about 10, at least about 20, at least about 30, at least about 40, at least about 50, at least about 100, at least about 200, at least about 500, at least about 1000, at least about 2000, at least about 5000, at least about 10000, at least about 50000, at least about 100000, at least about $2\times10^5$, at least about $5\times10^5$, at least about $1\times10^6$, at least about $2\times10^6$, at least about $5\times10^6$, at least about $1\times10^7$, at least about $2\times10^7$, at least about $5\times10^7$, at least about $1\times10^8$ or at least about $2\times10^8$ cells. In some instances, the composition may comprise at least $1.0\times10^7$, at least $1.0\times10^8$, at least $1.0\times10^9$, at least $1.0\times10^{10}$, at least $1.0\times10^{11}$ or at least $1.0\times10^{12}$ cells or even more cells.

The composite fibrous material can be adapted to control the release of the additive. For instance, the dry non-fibrous component may be crosslinked in order to slow the release of the additive.

EXAMPLES

The invention will now be illustrated by the following Examples.

Example 1

Reinforced PLGA Microfibres with High Molecular Weight 2200 kDa Hyaluronic Acid

Fabrication of Membranes

Reinforced membranes were co-spun using two nozzle heads. The first, a four-nozzle setup electrospun a solution of 23% 155 kg/mol PLGA (50:50 ratio of glycolide to lactide) in DMSO, and the second, a five-nozzle head electrosprayed a solution of 0.5% 2200 kDa hyaluronic acid in water and methanol (1:1 ratio).

Membranes were also electrospun without the hyaluronic acid component (hereinafter referred to as "no HA").

In more detail, for the manufacturing of the material by co-electrospinning-electrospraying, two polymer solutions were prepared. First, 23 wt % poly(d 1-lactide-co-glycolide) (50:50 ratio of lactide to glycolide, Mw 155 kg/mol) from Corbion (Supplier Code: PDLG 5010, Lot 1807002369) was dissolved in dimethyl sulfoxide (99.9%, Sigma Aldrich, Supplier Code: 276855, Lot STBJ2673). Second, 0.5 wt % (hereinafter referred to as "low HA") or 0.8 wt % (hereinafter referred to as "high HA") sodium hyaluronate (laboratory grade from Contipro, Supplier code: 600 01 15, Lot: 219-32749) was dissolved in a 1:1 mixture of deionised water and methanol (98.8% from Sigma Aldrich, supplier code: 32213, Lot: STBH4353). Both solutions were dissolved and homogenised on a roller mixer for at least 48 h at room temperature.

The device contained a fibrous and a dry non-fibrous component. For the fibrous component, the PLGA solution was delivered at a constant feed rate of 1.6 mL/h via a syringe pump using a four-nozzle head. The solution was vertically electrospun with an accelerating voltage of +20 kV DC-+25 kV.

For the dry non-fibrous component, the described sodium hyaluronate solution was delivered with a constant feed rate of 12 mL/h via a syringe pump using a 5-nozzle head. The solution was electrosprayed with an accelerating voltage of +13 kV DC-+16 kV. Temperature and relative humidity were kept constant (respectively at 25° C. and 40% RH) in a climate-controlled electrospinning machine. Components were collected on release paper sheets wrapped around a rotating collector positioned either 40 cm or 15 cm from the tip of the needle for the fibrous and dry non-fibrous component, respectively. The collector was rotated at 100 rpm. Longitudinal translation was also applied, using a programmable motorised stage with a translation speed of 40 mm/s. Electrospinning was performed for 3 hours.

Fibre diameter and scaffold morphology characterisation were performed by scanning electronic microscopy (SEM) using automated image characterisation of multiple images in order to determine the mean fibre diameter and the relative standard deviation. The FiberMetric software automatically identifies the location of the fibres within the captured SEM image and measures the diameter of each fibre 20 times at a specific location. Typically, around 100 such measurements are performed per image. The diameter of the fibres can alternatively be obtained via manual measurements and analysis of multiple SEM images.

The average fibre diameter of the fibres on the top layer was 2.2 μm with a standard deviation of 0.65 μm. The thickness of the sheet was measured using a digital micrometer. The average thickness of the material was 40 μm with a tolerance of ±20%.

The material sheet was dried in a vacuum oven at ~10 mbar for 16 hours at 40° C. to reduce the amount of residual solvent remaining from the fabrication process.

Some of the materials were subjected to plasma treatment. For instance, the surface of materials without HA was activated with oxygen plasma first before being exposed to acrylic acid plasma (this service was provided by Henniker Plasma).

Figure 1D:
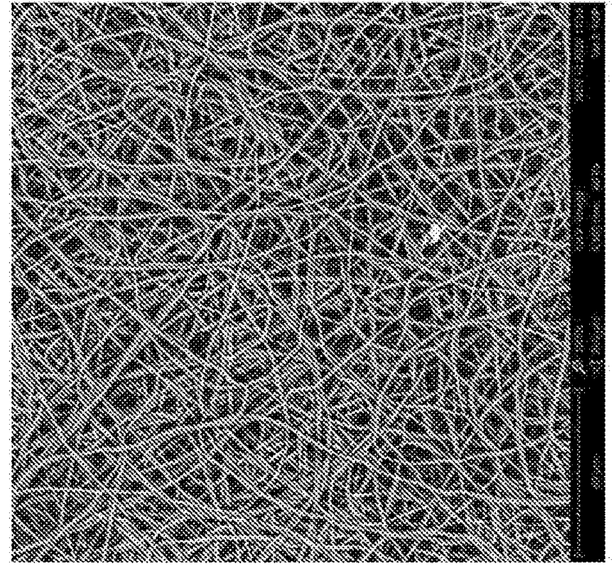
FIG. 1D shows scanning electron micrographs of a fibrous composite material according to the present invention comprising a PLGA membrane reinforced with low HA (left hand side), high HA (middle) and no HA (right hand side).
Figure 1D:
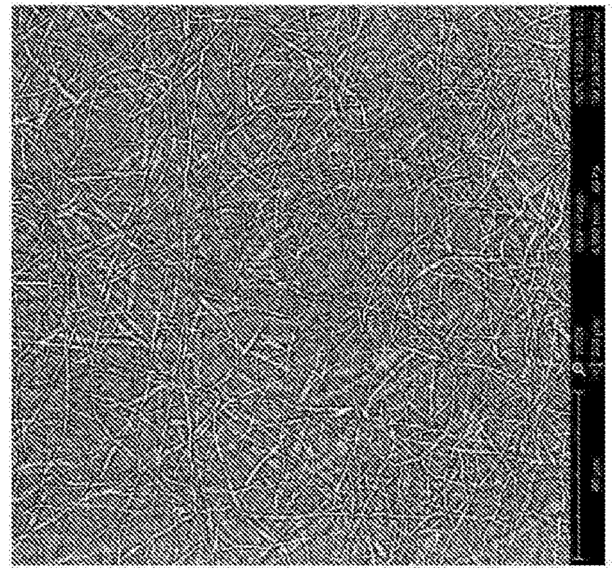
Figure 1D:
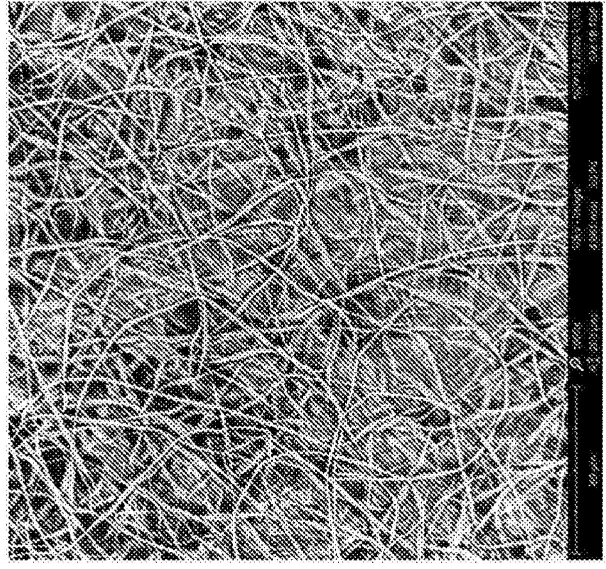
Figure 2A:
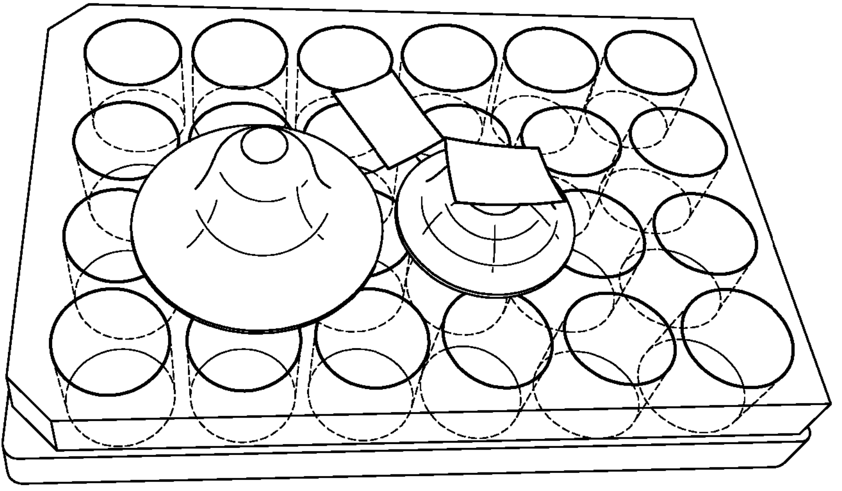
FIGS. 2A and 2B show the compliance assessment of the membranes formed from the fibrous composite material of the present invention with HA before and after wetting.
Figure 2B:
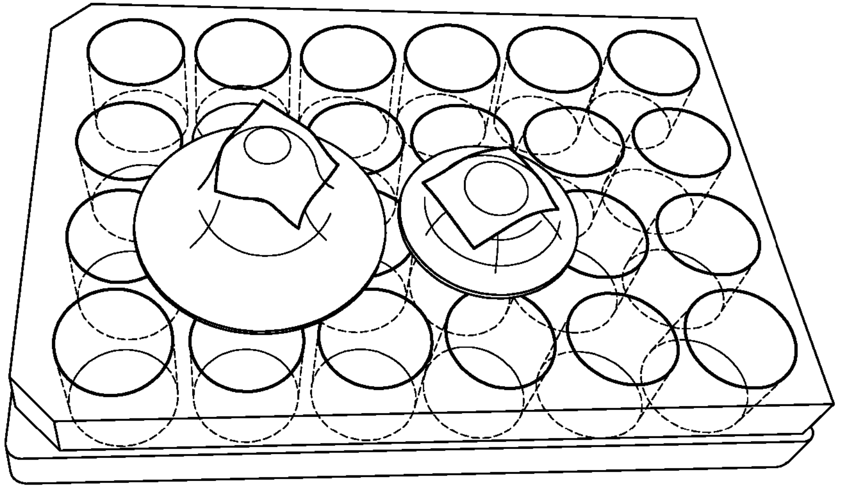

Scanning electron micrographs of the resulting fibrous composites were obtained (FIGS. 1A-D). The resultant material was easy to wet. Accordingly, no plasma treatment was required to wet the membranes containing hyaluronic acid (HA). Furthermore, FIG. 1D illustrates that the pores (voids or empty space) between the PLGA fibres was filled with HA, resulting in a much smoother surface than the material without HA. The appearance of the material with HA is much closer to the morphology of amniotic membrane (AM).

UV-Vis spectra on materials with and without HA were carried out. The samples were run on an Agilent Cary 5000 UV-vis-NIR spectrometer with a scan rate of 600 nm/min and 1 nm data interval. The scan range was 800-350 nm. The samples were held between two 20×20 mm glass coverslips and measured in transmission. Two glass coverslips were placed in the reference beam.

Figure 3A:
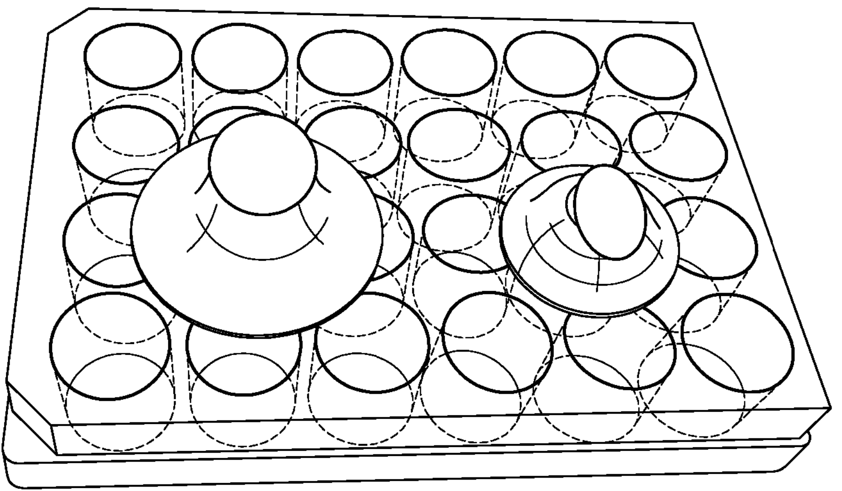
FIGS. 3A and 3B show the compliance assessment of the materials formed from the fibrous composite material without HA following plasma treatment and before wetting (FIG. 3A) and after wetting (FIG. 3B).
Figure 3B:
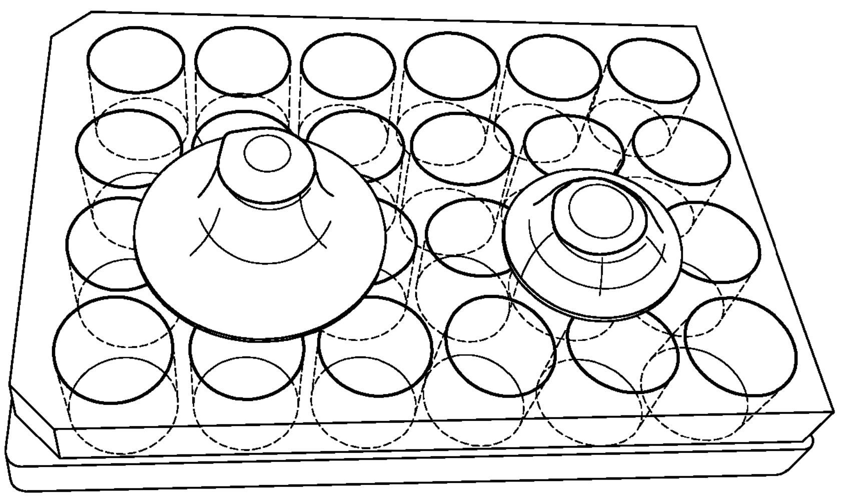
Figure 3C:
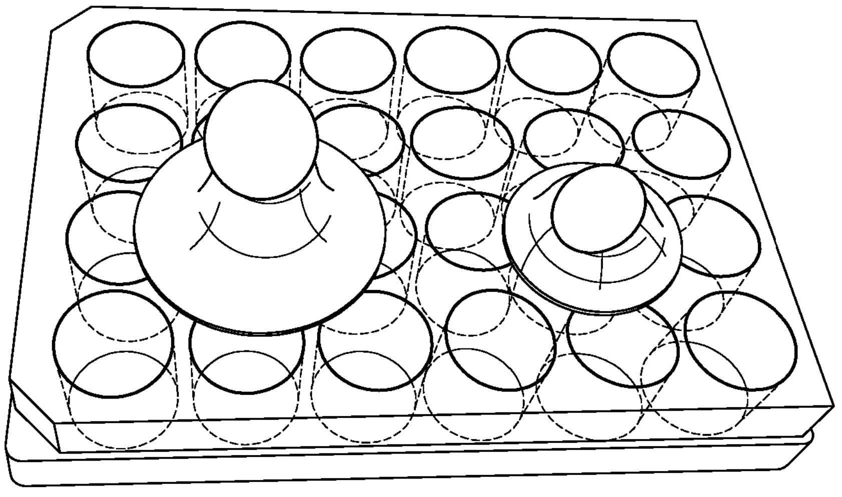
FIGS. 3C and 3D show the compliance assessment of the materials formed from the fibrous composite material without HA and without any plasma treatment: before wetting (FIG. 3C) and after wetting (FIG. 3D).
Figure 3D:
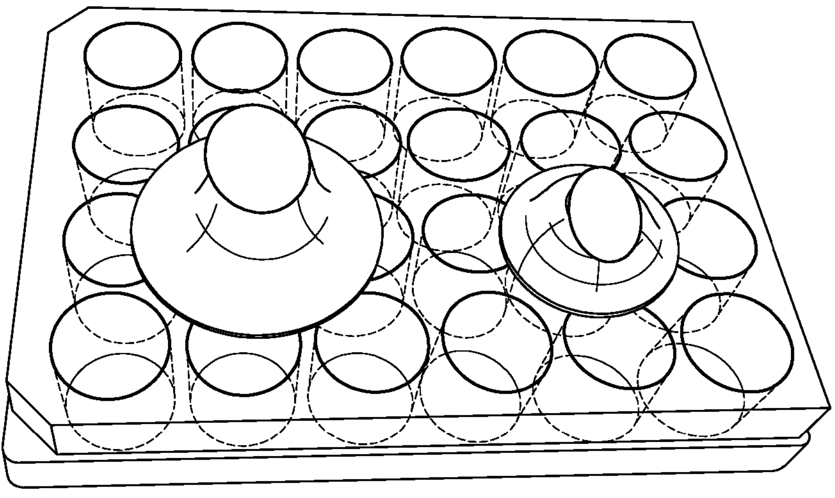
Figure 5A:
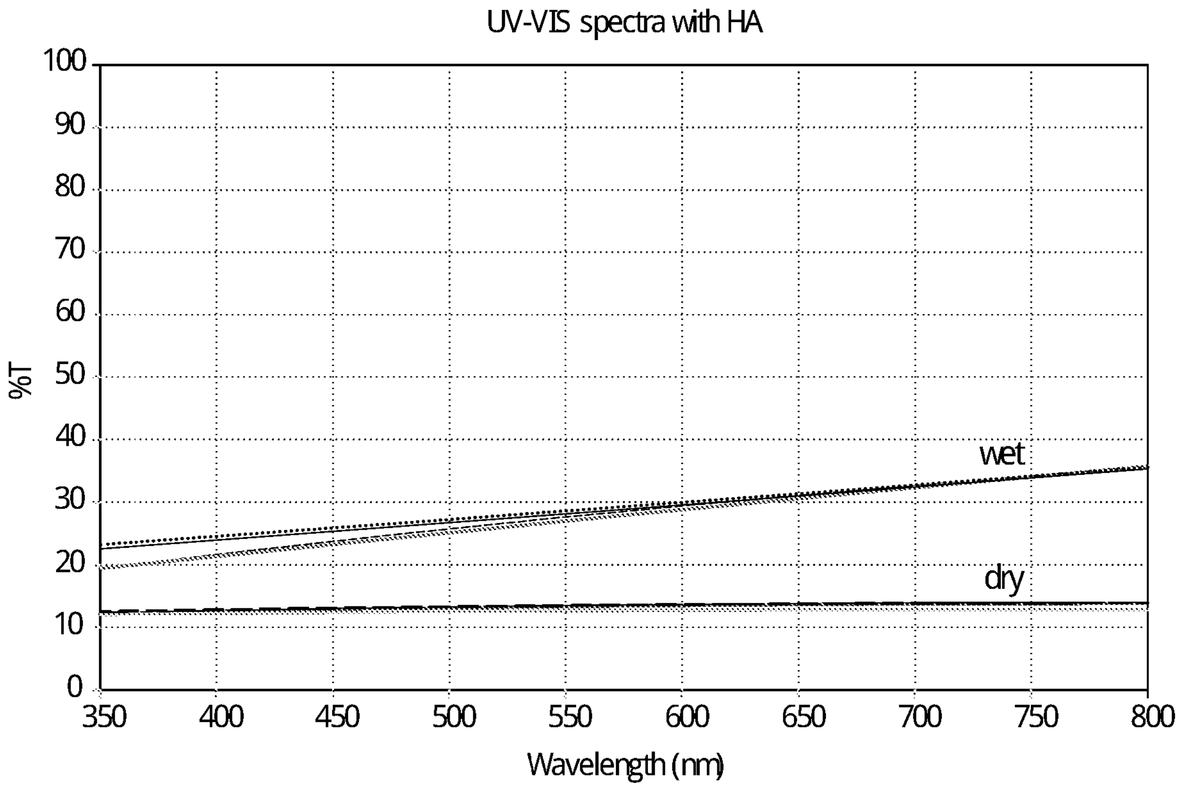
FIGS. 5A and 5B show UV-Vis spectra of materials with and without HA.
Figure 5B:
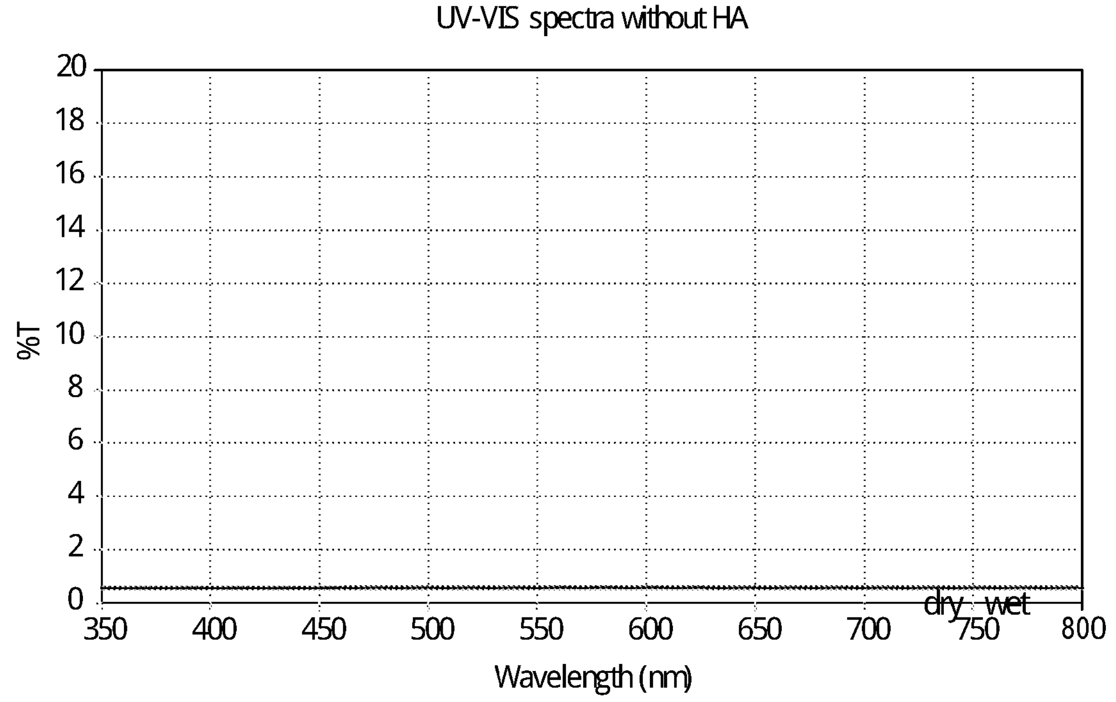

The material of the invention showed a high degree of transmittance (transparency)—see the UV-VIS spectra images in FIGS. 5A and 5B. Transparency improved drastically when wet in HA membranes vs. membranes without HA. This effect could only be achieved with plasma treatment in materials not comprising HA. This is illustrated by FIGS. 3A and 3B which show materials without HA, but with plasma treatment, versus FIGS. 3C and 3D which show the same materials without plasma treatment. FIG. 3D, the wet material, is almost identical to FIG. 3C, the dry material, showing no increase in transparency.

The elasticity of the membrane containing HA changed after wetting and membranes became significantly softer. The Young's modulus decreased from around 281 MPa before wetting to 38 MPa after wetting. Dry membranes started tearing when elongated by 37% of their original length but after wetting, membranes could be elongated up to 139%.

Tensile testing data are displayed in Table 1.

TABLE 1

Tensile testing data.

| | Specimen No. | Description | Modulus (MPa) | Ultimate Force (N) | Ultimate Stress (MPa) | Break Strain (%) |
|---|---|---|---|---|---|---|
| | 1 | Dry | 242 | 0.52 | 5.3 | 39.9 |
| | 2 | Dry | 322 | 0.56 | 5.63 | 34.4 |
| | 3 | Dry | 278 | 0.5 | 5.04 | 37.6 |
| Average | | | 280.67 | 0.53 | 5.32 | 37.30 |
| SD | | | 40.07 | 0.03 | 0.30 | 2.76 |
| | 1 | Wet | 31.10 | 0.25 | 2.56 | 142.00 |
| | 2 | Wet | 56.90 | 0.25 | 2.48 | 135.00 |
| | 3 | Wet | 25.20 | 0.23 | 2.35 | 139.00 |

TABLE 1-continued

| Tensile testing data. | | | | | | |
|---|---|---|---|---|---|---|
| | Specimen No. | Description | Modulus (MPa) | Ultimate Force (N) | Ultimate Stress (MPa) | Break Strain (%) |
| Average | | | 37.73 | 0.24 | 2.46 | 138.67 |
| SD | | | 16.86 | 0.01 | 0.11 | 3.51 |

Compliance testing was undertaken on the membranes formed from the fibrous composite materials (FIGS. 2A, 2B, 3A, 3B). Square (FIG. 2) and round membranes (FIG. 3) (low HA content) were positioned dry and wet on a round 3D surface corresponding to the size and shape of a rabbit's eye. Wet membranes adapted to the surface, whereas dry membranes did not. Furthermore, the wet membranes showed transparency where the surface of substrate could be seen through.

Slow dissolution of hyaluronic acid commenced immediately after membrane wetting, depositing a thin film of lubricant on the fibrous scaffold. The resulting membranes could be positioned on and moved across three-dimensionally shaped objects simulating a non-flat surface. The hand feel of the membranes was very similar to that of human tissue.

Figure 4A:
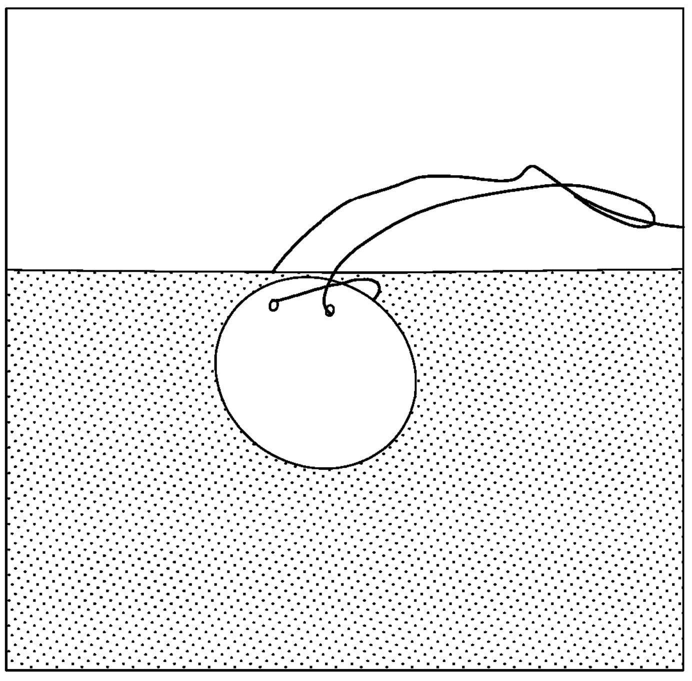
FIGS. 4A and 4B show the suturing of membranes formed from the fibrous composite material without HA and with HA.
Figure 4B:
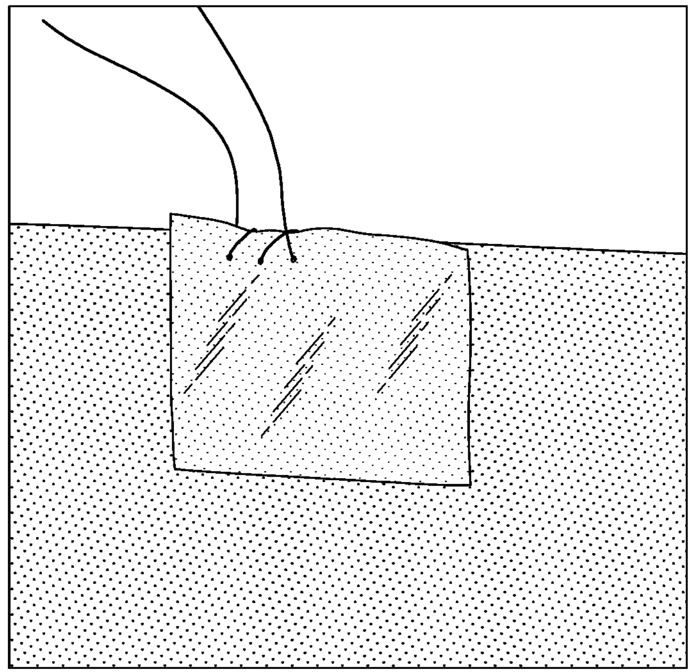

Tests for suturability were then undertaken (FIGS. 4A & 4B), which showed that when the membranes were sutured, puncture holes from the needle were observed on the membranes not containing hyaluronic acid. Where the membranes contained hyaluronic acid, the puncture holes were markedly smaller, facilitating fastening of the membrane in situ and improving its surgical appeal.

Example 2: Calculating the Relative Proportions of Fibrous and Non-Fibrous Components Low Loading of HA in Material:

12 mL of 0.5 wt % HA solution is deposited per hour where the deposition contains 0.06 mg of HA (12*0.5%=0.06 mg).

1.6 mL of PLGA solution is deposited per hour where the deposition contains 0.368 mg PLGA (1.6*23%=0.368 mg).

The proportion of HA in the device is 0.06/(0.368+0.06)*100=14%.

The proportion of PLGA in the device is 0.368/(0.368+0.06)*100=86%.

High Loading of HA in Material:

12 mL of 0.8 wt % HA solution is deposited per hour where the deposition contains 0.096 mg of HA (12*0.8%=0.096 mg).

1.6 mL of PLGA solution is deposited per hour where the deposition contains 0.368 mg PLGA (1.6*23%=0.368 mg).

The proportion of HA in the device is 0.096/(0.368+0.096)*100=21%.

The proportion of PLGA in the device is 0.368/(0.368+0.096)*100=79%.

Example 3: Water Content in the Material

In this Example, the water of materials according to the invention (made as per the method in Example 1) was analysed. 5 mL of methanol were added to 0.05 g of material in a vial, and water was then extracted from samples of material by rolling the vial for 2 hours. The solution was then analysed for water content using a Schott Titroline alpha titrator.

A blank methanol sample was also analysed at the same time to blank correct the results obtained for the samples.

The water content measured was on average 6% throughout the samples analysed.

Example 4: Assessment of Cell Morphology on the Material of the Invention

Immortalised human corneal keratinocytes (IHCKs) were cultured on materials according to the invention including low and high loadings of HA. Membranes were compared to a membrane containing no HA. All membranes in this assessment were secured in cell crown inserts and cells were seeded in numbers of $4.5\times10^5$ per insert in a 24-well plate. After 24 h, 72 h and 7 days in culture, cells were fixed and samples dehydrated for scanning electron microscopy (SEM) analysis.

Figures 6A, 6B:
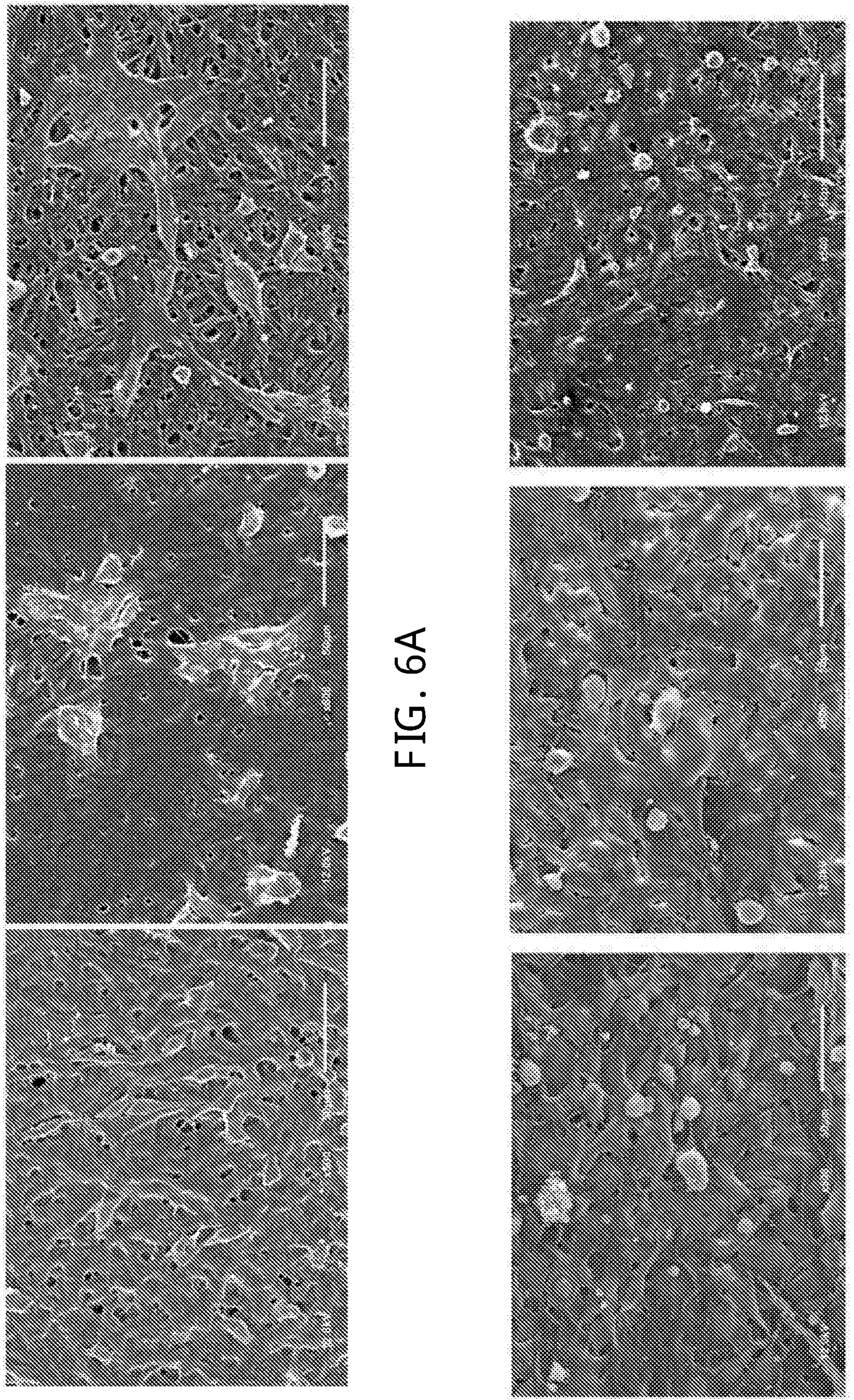
FIGS. 6A and 6B show scanning electron micrographs of Immortalised Human Corneal Keratinocytes (IHCKs) on the material according to the invention with low (left image) and high (centre image) HA loading and no HA content (right image) after 24 hours and 7 days in culture, respectively.

FIGS. 6A and 6B illustrate IHCKs on the inventive material with low (left image) and high (centre image) HA loading and no HA content (right image) after 24 hours and 7 days in culture, respectively. Even after 24 h of culture, cells on low and high HA loaded materials showed an in vivo-like morphology with cells uniformly covering a majority of the membranes (FIG. 6A). After 7 days, cells on the invention with low and high HA content, exhibited confluency with early signs of cell differentiation and stratification (FIG. 6B). In comparison, cells on membranes without HA showed an atypical behaviour with round-shaped morphology after 24 h and uneven coverage of the substrate. Even after 7 days in culture, confluency was not fully reached. Earlier cell differentiation and stratification together with faster confluency is expected to be advantageous in the ophthalmic and wound care settings, resulting in quicker barrier formation and quicker restoration of a healthy epithelium.

Figure 6C:
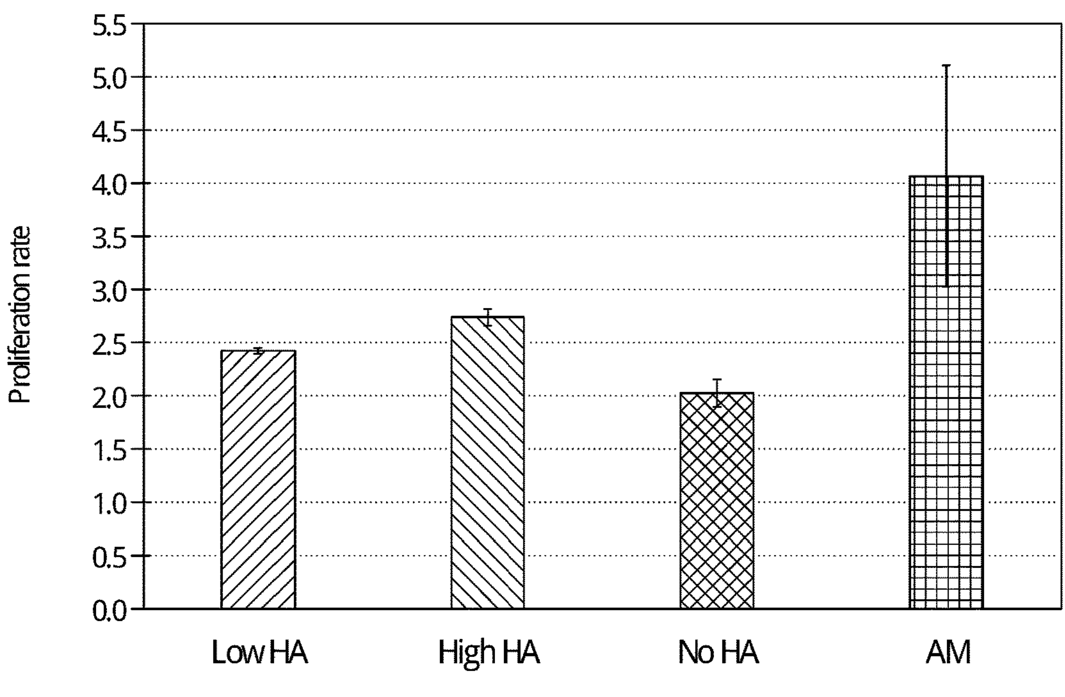
FIG. 6C shows the rate of proliferation of epithelial cells grown on materials with low, high and no HA content and compared to amniotic membrane.

The proliferation rate of the cells discussed above in relation to FIGS. 6A and 6B was measured. FIG. 6C shows the proliferation rate expressed as a fold increase in DNA from 24 h to 7 days. Cells proliferated/grew faster on HA-containing material in comparison to materials lacking HA. This suggests that a wound might regenerate/close faster if material with HA is used in comparison to a material lacking HA.

Example 5: Protein Marker Expression of Epithelial Cells on the Invention Vs. Amniotic Membrane Immortalised human corneal keratinocytes (IHCKs) were cultured on membranes as described in Example 4. Membranes containing low and high HA concentrations were compared to membranes without the addition of HA and human amniotic membrane (HAM). At three different time intervals (24 h, 3 days and 7 days) expression of the following markers was investigated via immunofluorescence staining:

| Marker | Epitope | Relevance |
|---|---|---|
| ZO-1 | Zonula Occludens (tight junction) | Indicator for the formation of a de novo barrier layer by the IHCKs |
| pFAK | Focal Adhesion Kinase | Indicator for the ability of IHCKs to adhere to the invention |
| C12 | Cytokeratin 12 | Structural marker indicating early differentiation of IHCKs into correct cornea epithelial phenotype |
| C19 | Cytokeratin 19 | Structural marker indicating late differentiation of IHCKs into correct cornea epithelial phenotype |

The following table summarises the occurrence of the markers mentioned above in ICHKs cultured on the invention with low and high HA loading, material without HA and AM (+ stands for marker expression; – stands for no marker expression):

| | | Low HA | High HA | No HA | AM |
|---|---|---|---|---|---|
| 24 h | CK12 | + | + | + | No data |
| | CK19 | + | — | — | No data |
| | ZO1 | + | + | — | No data |
| | pFAK | + | + | + | No data |
| 3 d | CK12 | — | — | — | No data |
| | CK19 | + | + | — | No data |
| | ZO1 | + | + | — | No data |
| | pFAK | + | + | — | No data |
| 7 d | CK12 | — | — | — | — |
| | CK19 | + | + | + | + |
| | ZO1 | + | + | — | + |
| | pFAK | — | + | — | — |

At the 24-hour timepoint, cells adhered to all of the electrospun materials. However, tight junctions (indicated by expression of ZO-1) only formed on HA containing membranes. The results suggest that materials of the invention containing HA support cell differentiation better than materials falling outside of the invention without HA.

At the 3-day timepoint, cells on the HA-loaded materials had progressed to a differentiated phenotype, whereas materials without the HA had not.

At the 7-day timepoint, cells on materials according to the invention (with HA) now showed a differentiated phenotype but cells on materials without HA were still not confluent and did not possess tight junctions. Focal contact between cells and substrate was no longer visible on low HA materials suggesting that multiple cell layers had formed. ICHKs on low HA membranes showed similar results to cells on amniotic membrane (AM).

Improved barrier formation as shown by the markers above is indicative of improved performance in the in vivo setting, where faster wound closure can be expected. Improved barrier formation in the eye would have the direct effect of enhancing the host's defence mechanisms against pathogens.

Example 6: Response of Monocyte-Derived Dendritic Cells on Materials According to the Invention This study focused on analysing the potential of materials according to the invention to influence a key immunological process namely the activation of dendritic cells (DC). DCs play a key role in the recognition of invading pathogens and activating the immune system for defence. The HLA-DR marker is a predictor of how macrophages would react to the materials. The outcome of this study holds predictive value for how macrophages would be expected to respond to the materials of the invention. Macrophages and dendritic cells are both of the same precursor lineage (monocytes), and studies showing that conditions that favour a more tolerogenic DC phenotype may suggest that macrophages behave in a similar manner.

Immature dendritic cells (DC) were generated from THP-1 human monocyte cells (cell line) by incubation with GMCSF and IL4 in RPMI-1640 medium for 7 days. DCs were added to either low, high or no-HA materials.

Immature DCs grown in presence of low, high and no HA materials were exposed to LPS and various controls to induce DC maturation. Maturation was measured by flow cytometric analysis of CD11c, HLA-DR, CD86 positive cells.

Figure 7:
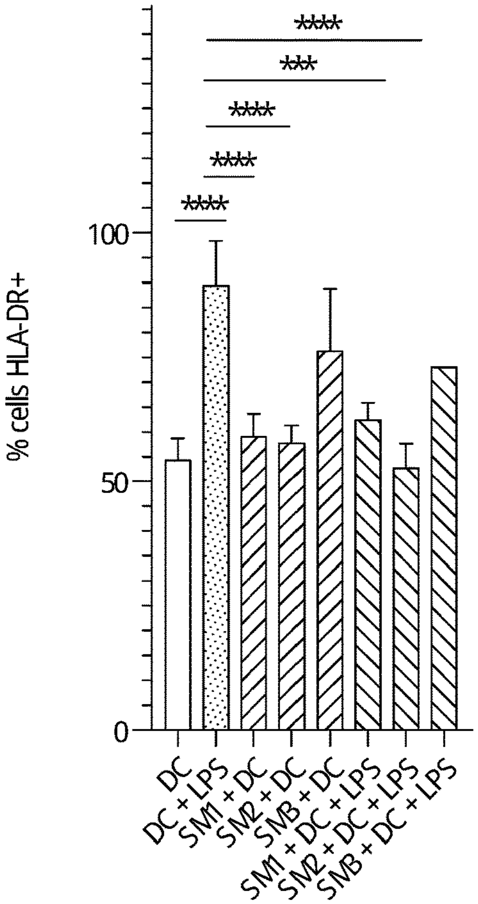
FIG. 7 shows the response of dendritic cells (DCs) to lipopolysaccharide (LPS).

FIG. 7 illustrates the response of DCs to LPS. Exposure of DCs to LPS significantly increased the expression of HLA-DR. DCs exposed to materials according to the invention with either low or high HA (SM1 and SM2) showed no increase in HLA-DR expression and significantly lower expression vs LPS treated DCS. DCs in presence of non-HA treated materials (SM3) however displayed an increased number of HLA-DR+ cells. LPS stimulated DCs cultured with materials according to the invention with low or high HA displayed a reduced stimulation whilst DCs grown together with non-HA treated materials had higher levels of HLA-DR positive cells.

The results show that materials containing HA showed significant benefits over those not containing HA. The addition of HA to the materials is expected to result in a lower inflammatory response in vivo.

What is claimed is:

1. A fibrous composite material for ophthalmic use comprising:

a nonfibrous component having a water content of less than 10 wt. %; and

50% to less than 90% by weight of a fibrous component comprising a porous scaffold of a plurality of electrospun polymeric fibers; and wherein the nonfibrous component is a linear or branched, water-soluble, synthetic, or natural polymer dispersed within pores of the porous scaffold wherein the porosity of the scaffold is at least 50%, and wherein the volume proportion of the pores filled by the non-fibrous component is in the range 10-30%.

2. The fibrous composite material of claim 1 wherein the nonfibrous component comprises a naturally derived polymer and proteins.

3. The fibrous composite material of claim 1 wherein the nonfibrous component comprises hyaluronic acid.

4. The fibrous composite material of claim 1 wherein the nonfibrous component has a water content less than 7 wt. %.

5. The fibrous composite material of claim 1 wherein the fibrous component comprises at least 60% by weight of the fibrous composite material.

6. The fibrous composite material of claim 1 wherein the fibrous component comprises poly(L-lactide); poly(glycolic acid); polyhydroxybutyrate; polystyrene; polyethylene; polypropylene; poly(ethylene oxide); a poly(ester urethane); poly(vinyl alcohol); polyacrylonitrile; polylactide; polyglycolide; polyurethane; polycarbonate; polyimide; polyamide; aliphatic polyamide; aromatic polyamide; polybenzimidazole; poly(ethylene terephthalate), poly[ethylene-co-(vinyl acetate)]; poly(vinyl chloride); poly(methyl methacrylate); poly(vinyl butyral); poly(vinylidene fluoride); poly(vinylidene fluoride-co-hexafluoropropylene); cellulose acetate; poly(vinyl acetate); poly(acrylic acid); poly(methacrylic acid); polyacrylamide; polyvinylpyrrolidone; poly (phenylene sulfide); hydroxypropylcellulose; polyvinylidene chloride, polytetrafluoroethylene, a polyacrylate, a polymethacrylate, a polyester, a polysulfone, a polyolefin, polysilsesquioxane, silicone, epoxy, cyanate ester, a bismaleimide polymer; polyketone, polyether, polyamine, polyphosphazene, polysulfide, an organic/inorganic hybrid polymer or a copolymer thereof; or a blend thereof.

7. The fibrous composite material of claim 1 wherein the fibrous component comprises poly(lactide-co-glycolide).

8. The fibrous composite material of claim 1 wherein the fibrous component is not covalently bound to the nonfibrous component.

9. The fibrous composite material of claim 1 wherein the fibers have a diameter in the range of 500 nm to 10 μm and/or a length of greater than 1 mm.

10. The fibrous composite material of claim 1 further comprising one or more additives.

11. The fibrous composite material of claim 10 wherein the one or more additives are selected from vitamin D, vitamin E, ectoine, and a hyaluronate salt.

12. The fibrous composite material of claim 1 wherein the nonfibrous component is not crosslinked.

13. The fibrous composite material of claim 2 wherein the naturally derived polymer is selected from hyaluronic acid, starch, dextran, heparin, chondroitin sulfate, dermatan sulfate, heparan sulfate, keratan sulfate, dextran sulfate, pentosan polysulfate, and chitosan.

14. The fibrous composite material of claim 3 wherein the hyaluronic acid has a molecular weight of more than 500 kDa.

15. The fibrous composite material of claim 4 wherein the nonfibrous component has a water content less than 5 wt. %.

16. The fibrous composite material of claim 5 wherein the fibrous component comprises at least 70% by weight of the fibrous composite material.

17. The fibrous composite material of claim 16 wherein the fibrous component comprises at least 80% by weight of the fibrous composite material.

18. The fibrous composite material of claim 10 wherein the one or more additives are selected from therapeutics and active ingredients.

19. The fibrous composite material of claim 18 wherein the therapeutics and/or active ingredients are selected from vitamins, antibiotics, steroids, miotics, antifungal agents, antiangiogenic agents, anti-inflammatory agents, antiviral, lubricants, and proteins.

20. A process for making a fibrous composite material according to claim 1, comprising simultaneously depositing the nonfibrous component while electrospinning the plurality of electrospun polymeric fibers to form the fibrous composite material on a collector.

21. The process of claim 20 comprising spraying a solution comprising a solvent and the nonfibrous component wherein the solvent is selected from 1-methyl-2-pyrrolidinone, 1-pentanol, 2-ethoxyethanol, 2-ethoxyethyl acetate, 2-nitropropane, 2,2,2-trifluoroethanol, acetic acid, acetone, acetonitrile, aniline, butanol, carbon tetrachloride, chloroform, cyclohexanone, di(ethylene glycol), diacetone alcohol, dichloroethane, dichloromethane, diethyl ether, diethylene glycol monoethyl ether, diisopropyl ether, dimethylacetamide, dimethylformamide, dimethyl sulfoxide, dioxane, ethanediol, ethanol, ethyl acetate, formic acid, glycerol, hexafluoropropan-2-ol, isopropanol, methanol, methyl acetate, methyl ethyl ketone, morpholine, n-butyl acetate, n-propanol, propylene carbonate, tetrahydrofuran, trifluoroacetic acid, water, or a mixture thereof.

22. The process of claim 20 wherein a solvent used to electrospin the plurality of polymeric fibers is selected from the group consisting of: 1-methyl-2-pyrrolidinone, 1-pentanol, 2-ethoxyethanol, 2-ethoxyethyl acetate, 2-nitropropane, 2,2,2-trifluoroethanol, acetic acid, acetone, acetonitrile, aniline, butanol, carbon tetrachloride, chloroform, cyclohexanone, di(ethylene glycol), diacetone alcohol, dichloroethane, dichloromethane, diethyl ether, diethylene glycol monoethyl ether, diisopropyl ether, dimethylacetamide, dimethylformamide, dimethyl sulfoxide, dioxane, ethanediol, ethanol, ethyl acetate, formic acid, glycerol, hexafluoropropan-2-ol, isopropanol, methanol, methyl acetate, methyl ethyl ketone, morpholine, n-butyl acetate, n-propanol, propylene carbonate, tetrahydrofuran, trifluoroacetic acid, water, and mixtures thereof.

23. A method of treatment of a patient in need thereof having a disease, the method comprising:

administering to the patient a fibrous composite material according to claim 1, wherein at least 50% by weight of the fibrous composite material is the fibrous component.

24. The method of claim 23 wherein the disease is an ocular defect or disorder, preferably wherein the ocular defect or disorder is selected from persistent epithelial defect, ocular complications associated with Stevens-Johnson syndrome, primary/recurrent pterygia, cicatricial pemphigoid and conjunctival forniceal reconstruction, corneal ulcers, corneal erosion, acute chemical/thermal burns, postinfectious keratitis (herpetic, vernal, bacterial), pinguecula, symblepharon, conjunctivoplasty, or painful bullous keratopathy.

* * * * *